United States Patent [19]

Bloch

[11] 3,953,523

[45] Apr. 27, 1976

[54] PROCESS FOR THE PREPARATION OF N-ALKYL-SUBSTITUTED HYDROXYPOLYALKOXYMETHYLCYCLOHEXENES

[75] Inventor: Herman S. Bloch, Skokie, Ill.

[73] Assignee: Universal Oil Products Company, Des Plaines, Ill.

[22] Filed: Nov. 4, 1974

[21] Appl. No.: 520,696

Related U.S. Application Data

[63] Continuation-in-part of Ser. No. 277,835, Aug. 3, 1972, Pat. No. 3,859,324.

[52] U.S. Cl............................................. 260/611 B
[51] Int. Cl.²......................................... C07C 41/02
[58] Field of Search.......... 260/611 B, 611 F, 617 R

[56] References Cited
UNITED STATES PATENTS 3,859,324   1/1975   Bloch................................. 260/457

Primary Examiner—Bernard Helfin
Attorney, Agent, or Firm—James R. Hoatson, Jr.; Raymond H. Nelson; William H. Page, II

[57] ABSTRACT

Non-ionic biodegradable detergents comprising n-alkyl-substituted hydroxypolyalkoxymethylcyclohexenes may be prepared by condensing butadiene with allyl alcohol, thereafter ring alkylating the resultant hydroxymethylcyclohexene with an olefin in the presence of a free-radical generating compound to form an alkyl-substituted hydroxymethylcyclohexene and alkoxylating this compound to form the desired product.

7 Claims, No Drawings

PROCESS FOR THE PREPARATION OF N-ALKYL-SUBSTITUTED HYDROXYPOLYALKOXYMETHYLCYCLOHEXENES

CROSS-REFERENCE TO RELATED APPLICATIONS

This application is a continuation-in-part of my copending Application Ser. No. 277,835 which was filed on Aug. 3, 1972, now U.S. Pat. No. 3,859,324, Jan. 7, 1975, all teachings of which are incorporated herein by reference thereto.

SPECIFICATION

This invention relates to a process for preparing non-ionic biodegradable detergents. More specifically, the invention is concerned with a novel method comprising a series of steps whereby n-alkyl-substituted hydroxypolyalkoxymethylcyclohexenes are formed.

One of the major problems which is prevalent in population centers throughout the world is the disposal of sewage containing detergents dissolved therein. Such disposal problems are especially trying in the case of branch-chained alkylaryl detergents. These detergents produce stable foams in hard or soft waters in such large quantities that the foam clogs sewage treatment facilities, and destroys the bacteria which are necessary for proper sewage treatment. In many rivers, streams, lakes, etc., which act as a water supply for the aforesaid population centers, there are found these unwanted foams and suds. As hereinbefore set forth, the presence of these unwanted foams or suds is due in many instances to the use of detergents which are non-biodegradable in nature and which will not break down by bacterial action thereon. The non-biodegradable nature of these detergents is due to the fact that the alkyl side chain of the molecule is in many instances highly branched and therefore not readily attacked by the organisms which would ordinarily destroy the molecule. In contradistinction to this, the use of straight chain alkyl substituents on the ring will permit the detergents to be destroyed and therefore foams or suds will not build up on the surface of the water.

It is therefore an object of this invention to provide a process for the production of detergents which show biodegradability in both urban and rural sewage disposal systems.

In one aspect an embodiment of this invention resides in a process for the preparation of a biodegradable detergent which comprises the steps of: (a) condensing butadiene with allyl alcohol in a Diels-Alder reaction at a temperature in the range of from about 50° to about 190° C. and a pressure in the range of atmospheric to about 100 atmospheres to form hydroxymethylcyclohexene; (b) ring alkylating said hydroxymethylcyclohexene with a 1-alkene in the presence of an organic peroxy free-radical generating compound and hydrogen chloride at a temperature at least as high as the decomposition temperature of said free-radical generating compound; (c) alkoxylating the resultant n-alkyl-substituted hydroxymethylcyclohexene with an alkoxylating agent selected from the group consisting of ethylene oxide and propylene oxide at a temperature in the range of from about 20° C. to about 125° C. and a pressure in the range of from about 50 to about 1000 pounds per square inch to form an n-alkyl-substituted hydroxypolyalkoxymethylcyclohexene; and (d) recovering said n-alkyl-substituted hydroxypolyalkoxymethylcyclohexene.

A specific embodiment of this invention is found in a process for the preparation of a biodegradable detergent which comprises the steps of condensing butadiene with allyl alcohol at a temperature in the range of from about 50° to about 190° C. and a pressure in the range of from atmospheric to about 100 atmospheres, ring alkylating the resultant hydroxymethylcyclohexene with 1-octene in the presence of di-t-butyl peroxide and hydrogen chloride at a temperature at least as high as the decomposition temperature of said di-t-butyl peroxide, alkoxylating the resultant n-octyl hydroxymethylcyclohexene with ethylene oxide at a temperature in the range of from about 20° to about 125° C. and a pressure in the range of from about 25 to about 1000 pounds per square inch in the presence of an acidic or basic catalyst and recovering the resultant n-octyl hydroxypolyethoxymethylcyclohexene.

Other objects and embodiments will be found in the following further detailed description of the present invention.

As hereinbefore set forth, the present invention is concerned with a process for the preparation of detergents which are biodegradable in nature. In addition, the present invention also contemplates the preparation of detergents which are non-ionic or anionic in nature, the process for preparing these compounds being effected in a series of steps. In the first step of the reaction, butadiene is condensed with allyl alcohol in a Diels-Alder type condensation to give 4-hydroxymethylcyclohexene. The Diels-Alder condensation is effected at elevated temperatures, usually in the range of from about 50° to about 190° C. and at a pressure ranging from atmospheric to about 100 atmospheres. The reaction pressure may be afforded by the autogenous pressure of the butadiene or by a combination of butadiene and a substantially inert gas such as nitrogen or argon, the amount of pressure which is utilized being that which is sufficient to maintain at least a portion of the reactants in the liquid phase.

The 4-hydroxymethylcyclohexene which has been prepared according to the above paragraph is recovered and selectively alkylated utilizing an olefinic hydrocarbon as the alkylating agent. The selective alkylation in which the alkyl substituent is positioned on the ring rather than on the side chain is effected by treating the reactants in the presence of a free-radical generating compound and hydrogen chloride. In the preferred embodiment of the invention, the olefinic hydrocarbon which is utilized as the alkylating agent will comprise a 1-alkene containing from 3 to about 20 carbon atoms in length and preferably from about 6 to about 14 carbon atoms. By utilizing the 1-alkene and an alkylation catalyst comprising a free-radical generating compound and a promoter comprising hydrogen chloride, it is possible to obtain a normal alkyl side chain on the cyclohexene ring rather than a secondary alkyl side chain which would result if the alkylation were effected in the presence of an acidic catalyst of the Friedel-Crafts type or sulfuric acid, etc. Specific examples of the alpha-olefinic hydrocarbons which are utilized as alkylating agents include propene, 1-butene, 1-pentene, 1-hexene, 1-heptene, 1-octene, 1-nonene 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, etc.

The catalysts which are used in this step of the invention will include peroxy compounds, containing the bivalent radical —O—O—, which decomposes to form free radicals which initiate the general reaction and are capable of inducing the condensation of the hydroxymethylcyclohexene with the 1-alkene. Examples of these catalysts include the persulfates, perborates, percarbonates of ammonium and of the alkali metals, or organic peroxy compounds. The organic peroxy compounds constitute a preferred class of catalysts for use in the invention and include peracetic acid, persuccinic acid, methyl ethyl ketone peroxide, methyl isobutyl ketone peroxide, acetyl peroxide, dipropionyl peroxide, di-t-butyl peroxide, butyryl peroxide, lauroyl peroxide, benzoyl peroxide, tetralin peroxide, urea peroxide, t-butyl perbenzoate, t-butyl hydroperoxide, methylcyclohexyl hydroperoxide, cumene hydroperoxide, diisopropylbenzene hydroperoxide, etc. Mixtures of peroxy compound catalysts may be employed or the peroxy compound catalyst may be utilized in admixture with various diluents. Thus, organic peroxy compounds which are compounded commercially with various diluents which may be used include benzoyl peroxide compounded with calcium sulfate, benzoyl peroxide compounded with camphor, phthalate esters, etc. Only catalytic amounts (less than stoichiometric amounts) need be used in the process.

The alkylation of the hydroxymethylcyclohexene with the 1-alkene is effected at elevated reaction temperatures which should be at least as high as the initial decomposition temperature of the free-radical generating catalyst, such as the peroxide compound, in order to liberate and form free radicals which promote the reaction. In selecting a particular reaction temperature for use in the process of the present invention, two considerations must be taken into account. First sufficient energy by means of heat must be supplied to the reaction so that the reactants, namely, the hydroxymethylcyclohexene and the 1-alkenes will be activated sufficiently for condensation to take place when free radicals are generated by the catalyst. Second, free-radical generating catalysts such as peroxy compounds, particular organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 11 hours at 125° C., 4 hours at 135° C., and 1.5 hours at 145° C. A reaction system temperature must then be selected so that the free-radical generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for condensation. When the half life of the free-radical generating catalyst is greater than 10 hours, radicals are not generated at a sufficient rate to cause the reaction of the process of the present invention to go forward at a practically useful rate. Thus the reaction temperature may be within the range of from about 50° to about 300° C. and at least as high as the decomposition temperature of the catalyst, by which is meant a temperature such that the half life of the free-radical generating catalyst is not greater than 10 hours. Since the half life for each free-radical generating catalyst is different at different temperatures, the exact temperature to be utilized in a particular reaction will vary. However, persons skilled in the art are well acquainted with the half life vs. temperature data for different free-radical generating catalysts. Thus it is within the skill of one familiar with the art to select the particular temperature needed for any particular catalyst. However, the operating temperatures generally do not exceed the decomposition temperature of the catalyst by more than about 100° C. since free-radical generating catalysts decompose rapidly under such conditions. For example, when a free-radical generating catalyst such as t-butyl perbenzoate is used, having a 10 hour, 50% decomposition temperature of approximately 105° C., the operating temperature of the process is from about 105° to about 205° C. When di-t-butyl peroxide having a decomposition temperature of about 125° C. is used, the process is run at a temperature ranging from about 125° to about 225° C. Higher reaction temperatures may be employed, but little advantage is gained if the temperature is more than the hereinbefore mentioned 100° C. higher than the 10 hour, 50% decomposition temperature of the catalyst. The general effect of increasing the operating temperature is to accelerate the rate of condensation reaction of the hydroxymethylcyclohexene with the 1-alkenes. However, the increased rate of reaction is accompanied by certain amounts of decomposition. In addition to the elevated temperatures which are utilized, the reaction may also be effected at elevated pressures ranging from 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure withstanding equipment to insure liquid phase conditions. In batch type operations, it is often desirable to utilize pressure-withstanding equipment to charge the reactants and the catalyst to the vessel and to pressure the vessel with 10 or 30 or 50 or more atmospheres of an inert gas such as nitrogen. This helps to ensure the presence of liquid phase conditions. However, when the mole quantity of reactants is sufficient, the pressure which they themselves generate at the temperature utilized is sufficient to maintain the desired phase conditions.

Furthermore, the concentration of the catalyst employed in this process may vary over a rather wide range but it is desirable to utilize low concentrations of catalysts such as from about 0.1% to about 10% of the total weight of the combined starting materials charged to the process. The reaction time may be within the range of from less than 1 minute to several hours, depending upon temperature and the half life of the catalyst. Generally speaking, contact times of at least 10 minutes are preferred.

In addition to the free-radical generating catalyst, the alkylation is also effected in the presence of a hydrogen chloride compound. The hydrogen chloride compound is used as a promoter for the reaction and also is used to prevent or inhibit telomerization, said telomerization being a polymerization reaction in which unwanted side reaction products may be formed. The hydrogen chloride may be present as anhydrous hydrogen chloride, as concentrated aqueous hydrochloric acid or as a more dilute aqueous solution of hydrochloric acid, the hydrochloric acid being present in an amount of from 5% to about 38% in said aqueous solution.

The n-alkyl-substituted hydroxymethylcyclohexene is then subjected to an alkoxylation step to prepare non-ionic detergents having the general structure:

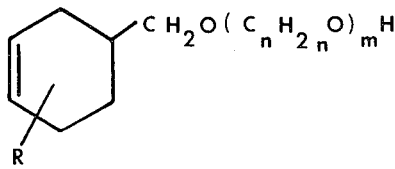

in which R is a normal alkyl radical containing from 3 up to about 20 carbon atoms, $n$ is 2 or 3 and $m$ is an integer ranging from 1 to about 50 and preferably in a range of from about 3 to about 20. The alkoxylation of the $n$-alkyl-substituted hydroxymethylcyclohexene is effected by treating the compound with an alkoxylating agent selected from the group consisting of ethylene oxide and propylene oxide in an amount sufficient to produce the desired number of alkoxy units in order that the values hereinbefore set forth for $m$ may be satisfied. In any event, a sufficient amount of alkylene oxide must be used to solubilize the product and maximize its surface active properties either with or without subsequent sulfation.

The alkoxylation is effected by treating the aforementioned compounds with ethylene oxide or propylene oxide at a temperature in the range of from about 20° (ambient) up to about 125° C. and at a pressure in the range of from about 50 to about 1000 pounds per square inch, the pressure being afforded by the alkoxylating agent. In addition, the alkoxylating reaction is effected in the presence of an acidic or basic catalyst. Examples of acids which may be employed will include mineral acids such as hydrochloric acid, sulfuric acid, phosphoric acid, etc., organic acids such as methanesulfonic acid, ethanesulfonic acid, benzenesulfonic acid, toluenesulfonic acid, acidic salts such as tin chloride, zinc chloride, ferric chloride, etc. Examples of basic catalysts which may be employed will include sodium carbonate, potassium carbonate, lithium carbonate, sodium acetate, potassium acetate, lithium acetate, sodium propionate, potassium propionate, lithium propionate, sodium hydroxide, potassium hydroxide, lithium hydroxide, the corresponding basic calcium compounds, magnesium compounds, etc. As hereinbefore set forth, a sufficient amount of alkoxylating agent will be used in order that the predetermined value for m in the above formula is satisfied. Therefore the alkoxylating agent will usually be present in the reaction mixture in a molar excess over that of the n-alkyl-substituted hydroxymethylcyclohexene, said molar excess usually being in a range of from 5:1 to about 50:1 moles of alkylene oxide per mole of substituted cyclohexene compound.

The process of this invention in which biodegradable detergents of the type hereinbefore set forth in greater detail are prepared may be effected in either a batch or continuous operation. When a batch type operation is used, a quantity of the allyl alcohol is placed in an appropriate apparatus such as an autoclave of the rotating or mixing type. The autoclave is sealed and the butadiene is charged thereto or, in an alternate method, a mixture of butadiene and an inert gas such as nitrogen is charged thereto until the desired operating pressure is reached. The autoclave is thereafter heated to the desired operating temperature within the range hereinbefore set forth and maintained thereat for a predetermined residence time which may range from 0.5 up to about 10 hours or more in duration. Upon completion of the desired residence time, heating is discontinued, the autoclave is allowed to return to room temperature, the excess pressure is vented and the reaction mixture is recovered therefrom. The hydroxymethylcyclohexene is separated from any unreacted allyl alcohol by conventional means such as distillation or by any other separation means known in the art and placed in a second reaction vessel along with a free-radical generating compound and the 1-alkene which is to be utilized as the alkylating agent. This second reaction vessel may be a flask provided with condensing means or an autoclave of the rotating or mixing type. In addition, a promoter comprising hydrogen chloride, either in gaseous form as hydrogen chloride or in aqueous form as hydrochloric acid, is added to the reactor which is thereafter heated to the desired operating temperature which, as hereinbefore set forth, is at least as high as the decomposition temperature of said free-radical generating compound. After maintaining the alkylation reaction at this temperature for a predetermined period of time which may range from about 0.5 up to about 10 hours, heating is discontinued, the reaction mixture is allowed to return to room temperature and the n-alkyl-substituted hydroxymethylcyclohexene is separated and recovered by conventional means.

The n-alkyl-substituted hydroxymethylcyclohexene is then treated with an alkoxylating agent to form the desired product. This treatment is accomplished by placing the substituted cyclohexene in an appropriate apparatus such as a rotating autoclave and the alkoxylating agent is added thereto in a predetermined molar excess so that the finished product will contain the requisite number of alkoxy units in the side chain. In addition, an acidic or basic catalyst of the type hereinbefore set forth in greater detail is also added to the apparatus which is thereafter heated to a predetermined operating temperature. After maintaining the apparatus and contents thereof at this temperature for a period of time which may range from about 0.5 up to about 10 hours or more, the apparatus and contents thereof are allowed to return to room temperature and the product is recovered therefrom and sent to storage.

It is also contemplated within the scope of this invention that the desired product may be prepared while employing a continuous manner of operation. When the continuous manner of operation is to be used, the starting materials comprising the allyl alcohol and butadiene are continuously charged to a reactor which is maintained at the proper operating conditions of temperature and pressure. After passage through this reactor for a predetermined period of time, the effluent is continuously withdrawn, subjected to a separation step whereby the unreacted allyl alcohol and butadiene are separated from the hydroxymethylcyclohexene and recycled to form a portion of the feed stock while the latter is continuously charged to an alkylation apparatus which is also maintained at the proper operating conditions of temperature and pressure. In addition, the 1-alkene, the free-radical generating compound and the hydrogen chloride promoter are also continuously charged to the apparatus through separate lines or, if so desired, one or more of the reactants may be admixed with another prior to entry into said reactor and the resulting mixture charged thereto in a single stream. After completion of the desired residence time in the alkylation apparatus, the reactor effluent is continuously withdrawn, again subjected to separation steps whereby unreacted starting materials, promoter and by-products are separated from the alkyl-substituted hydroxymethylcyclohexene. The unreacted starting materials are recycled to the apparatus to form a portion of the feed stock while the n-alkyl-substituted hydroxymethylcyclohexene is continuously charged to the alkoxylation reactor. In this reactor, the aforementioned cyclohexene is subjected to the action of an alkoxylating agent, said agent, either ethylene oxide or propylene oxide, being continuously charged to the reactor in a molar excess over the charge of the cyclohexene. In addition, the catalyst, either acidic or basic in nature, is also charged to the reactor through a separate line or, if so desired, it may be admixed with the carbinol feed and the resulting mixture charged thereto in a single stream. Upon completion of the desired residence time, the reactor effluent is withdrawn and subjected to separation steps known in the art whereby the desired final product may be separated and recovered while any unreacted starting materials are recycled to the reactor to form a portion of the feed stock.

The following examples are given to illustrate the process of the present invention which, however, are not intended to limit the generally broad scope of the present invention in strict accordance therewith.

EXAMPLE I

In this example, 58 grams (1.0 mole) of allyl alcohol is placed in the glass liner of a rotating autoclave. The liner is sealed into the autoclave and 54 grams (1.0 mole) of butadiene is charged thereto. The autoclave is then heated to a temperature of 125° C. and maintained thereat for a period of 4 hours, at the end of which time heating is discontinued, and the autoclave is allowed to return to room temperature. The autoclave is opened, the reaction mixture is recovered therefrom and subjected to fractional distillation whereby the desired product comprising 4-hydroxymethylcyclohexene is separated from any unreacted allyl alcohol and recovered.

The 4-hydroxymethylcyclohexene which is prepared according to the above paragraph is then placed in the glass liner of a rotating autoclave along with the alkylating agent comprising 1-octene, the charge stock consisting of a molar excess of the hydroxymethylcyclohexene over the 1-octene in a range of from about 1.5:1 to about 2:1 moles of hydroxymethylcyclohexene per mole of 1-octene. In addition, 7 grams of di-t-butyl peroxide and 20 grams of concentrated hydrochloric acid which acts as a promoter are also placed in the autoclave. The liner is sealed into the autoclave and nitrogen is pressed in until an initial operating pressure of 30 atmospheres is reached. Thereafter the autoclave and contents thereof are heated to a temperature of 130° C. and maintained in a range of from 130° to 140° C. for a period of 8 hours. At the end of the 8-hour period, heating is discontinued, the autoclave is allowed to return to room temperature and the excess pressure is discharged therefrom. The autoclave is then opened, the reaction mixture is recovered and subjected to fractional distillation, usually under reduced pressure, whereby the desired product comprising the n-octyl-substituted 4-hydroxymethylcyclohexene is separated from unreacted starting materials, acid, etc. and recovered.

The n-octyl-substituted hydroxymethylcyclohexene which is recovered according to the method set forth in the above paragraph is then placed in an autoclave and a catalytic amount of sodium carbonate is added to the reactor which is thereafter sealed. A molar excess of ethylene oxide comprising about 9 moles of ethylene oxide per mole of n-octyl-substituted hydroxymethylcyclohexene is then pressured in, and the autoclave is heated to a temperature of 50° C. At the end of the 4-hour period, heating is discontinued, the autoclave is allowed to return to room temperature, the excess pressure is discharged and the n-octyl hydroxypolyethoxymethylcyclohexene is recovered.

EXAMPLE II

In this example a mole proportion of allyl alcohol is placed in the glass liner of a rotating autoclave which is thereafter sealed and a mole proportion of butadiene along with a sufficient amount of nitrogen is pressed into the autoclave until an initial pressure of 30 atmospheres is reached. The autoclave and contents thereof are then heated to a temperature of 140° C. and maintained in a range of from 135° to 140° C. for a period of 4 hours. At the end of the 4-hour period, heating is discontinued, the autoclave is allowed to return to room temperature and the excess pressure is discharged therefrom. The autoclave is opened, the reaction mixture is recovered and subjected to fractional distillation under reduced pressure whereby the desired product comprising 4-hydroxymethylcyclohexene is separated and recovered.

The hydroxymethylcyclohexene which is prepared according to the above paragraph is then placed in the glass liner of a rotating autoclave along with 1-tetradecene, the hydroxymethylcyclohexene being present in a molar excess over the 1-tetradecene. In addition, a catalyst comprising 7 grams of di-t-butyl peroxide and a promoter comprising 20 grams of hydrochloric acid is also added to the liner. The liner is then sealed into the autoclave and nitrogen is pressed in until an initial operating pressure of 30 atmospheres is reached. The autoclave and contents thereof are then heated to a temperature of 130° C. and maintained in a range of from 130° to 140° C. for a period of 8 hours. At the end of this period, heating is discontinued, the autoclave is allowed to return to room temperature, the excess pressure is discharged and the autoclave is opened. After recovery of the reaction mixture, it is subjected to fractional distillation under reduced pressure whereby the n-tetradecyl-substituted 4-hydroxymethylcyclohexene is recovered.

The aforementioned n-tetradecyl-substituted hydroxymethylcyclohexene is placed in the glass liner of a rotating autoclave along with propylene oxide in a mole ratio of 10 moles of propylene oxide per mole of substituted cyclohexene. In addition, a catalytic amount of sodium carbonate is also added to the liner which is thereafter sealed into the autoclave and the resulting mixture heated to a temperature of 50° C. for a period of 4 hours. At the end of this time, heating is discontinued, the excess pressure is discharged and the desired biodegradable detergent comprising an n-tetradecyl hydroxypolypropoxymethylcyclohexene is recovered therefrom.

EXAMPLE III

In like manner, 58 grams of allyl alcohol is placed in the glass liner of a rotating autoclave which is thereafter sealed and 54 grams of butadiene is charged thereto. Following this, the autoclave is then heated to a temperature of 125° C. and maintained thereat for a period of 4 hours, at the end of which time heating is discontinued and the autoclave is allowed to return to room temperature. The autoclave is opened and the reaction mixture is recovered therefrom and subjected to fractional distillation under reduced pressure whereby the desired product comprising 4-hydroxymethylcyclohexene is separated from any unreacted starting materials and recovered.

Following this, the 4-hydroxymethylcyclohexene is placed in the glass liner of a rotating autoclave along with the alkylating agent comprising 1-decene, the said 4-hydroxymethylcyclohexene being in a molar excess over the 1--decene. In addition, 6 grams of benzoyl peroxide and 20 grams of concentrated hydrochloric acid are also placed in the autoclave. The liner is sealed into the autoclave, nitrogen is pressed in until an initial operating pressure of 30 atmospheres is reached and the autoclave and contents thereof are heated to a temperature of 80° C. The autoclave is maintained at a temperature in the range of from about 80° to about 90° C. for a period of 8 hours, at the end of which time heating is discontinued, the autoclave is allowed to return to room temperature and the excess pressure is discharged therefrom. The autoclave is then opened, the reaction mixture is recovered and subjected to fractional distillation under reduced pressure whereby the desired product comprising n-decyl hydroxymethylcyclohexene is separated from the unreacted starting materials and the hydrochloric acid and recovered.

The desired product is then prepared by placing the n-decyl-substituted hydroxymethylcyclohexene in an autoclave along with a catalytic amount of sodium carbonate. The reactor is then sealed and a molar excess of ethylene oxide comprising 10 moles of ethylene oxide per mole of n-decyl hydroxymethylcyclohexene is pressured in. The autoclave is then heated to a temperature of 50° C. for a period of 4 hours, following which heating is discontinued, the autoclave is allowed to return to room temperature, the excess pressure is discharged and n-decyl hydroxypolyethoxymethylcyclohexene is recovered therefrom.

EXAMPLE IV

In a manner similar to that set forth in the above examples, a mole proportion of allyl alcohol is reacted with a mole proportion of butadiene in a rotating autoclave which is heated to a temperature of 140° C. for a period of 4 hours. At the end of this 4-hour period, the autoclave and contents thereof are treated in a manner similar to that hereinbefore set forth whereby the desired product comprising 4-hydroxymethylcyclohexene is separated and recovered.

The 4-hydroxymethylcyclohexene is then placed in the glass liner of a rotating autoclave along with 1-tridecene, the hydroxymethylcyclohexene being in a molar excess of about 2 moles of the cyclohexene per mole of tridecene. In addition, the autoclave will also contain 7 grams of the catalyst comprising di-t-butyl peroxide and 20 grams of concentrated hydrochloric acid. After sealing the liner into the autoclave, nitrogen is pressed in until an initial operating pressure of 30 atmospheres is reached and thereafter the autoclave and contents thereof are heated to a temperature of 130° C., said autoclave and contents beng maintained in a range of from 130° to 140° C. for a period of 8 hours. At the end of this period, heating is discontinued, the autoclave is allowed to return to room temperature, the excess pressure is discharged and the autoclave is opened. The reaction mixture, after recovery from the autoclave, is subjected to fractional distillation under reduced pressure whereby the n-tridecyl hydroxymethylcyclohexene is recovered.

The n-tridecyl hydroxymethylcyclohexene is then placed in the glass liner of a rotating autoclave along with the alkoxylating agent comprising propylene oxide, the reactants being present in a mole ratio of 10 moles of propylene oxide per mole of substituted cyclohexene. In addition, a catalytic amount of sodium carbonate is also added to the liner of the autoclave which is thereafter sealed into the autoclave and the reaction mixture is heated to a temperature of 50° C. for a period of 4 hours. Following this, heating is discontinued, the excess pressure is discharged and the desired product comprising n-tridecyl hydroxypolypropoxymethylcyclohexene is recovered therefrom.

EXAMPLE V

In a manner similar to that set forth in the above examples, a mole proportion of allyl alcohol is reacted with butadiene in a rotating autoclave under an implied pressure of 30 atmospheres of nitrogen and a temperature of 140° C. for a period of 4 hours. At the end of this period, the autoclave and contents thereof are treated in a manner similar to that set forth in Example I above whereby the desired product comprising 4-hydroxymethylcyclohexene is separated and recovered.

The substituted cyclohexene is then placed in the glass liner of a rotating autoclave along with 1-dodecene in a mole ratio of 2 moles of substituted cyclohexene per mole of 1-dodecene. A catalyst comprising 6 grams of benzoyl peroxide and a promoter comprising 30 grams of concentrated hydrochloric acid are also added to the liner which is thereafter sealed into the autoclave. After nitrogen is pressed in until an initial operating pressure of 30 atmospheres is reached, the autoclave and contents thereof are then heated to a temperature of 80° C. After maintaining the autoclave at a temperature in the range of from 80° to 90° C. for a period of 8 hours, heating is discontinued, the autoclave is allowed to return to room temperature, the excess pressure is discharged and the autoclave is opened. The reaction mixture is recovered, subjected to fractional distillation and the desired product comprising n-dodecyl hydroxymethylcyclohexene is recovered therefrom.

In like manner the n-dodecyl hydroxymethylcyclohexene is alkoxylated by placing it in the glass liner of a rotating autoclave along with ethylene oxide in a mole ratio of 12 moles of ethylene oxide per mole of substituted cyclohexene. After treatment in the autoclave for a period of 4 hours at a temperature of 50° C. in the presence of a catalytic amount of sodium carbonate, heating is discontinued, the autoclave is allowed to return to room temperature and opened. The desired biodegradable detergent comprising n-dodecyl hydroxypolyethoxymethylcyclohexene is recovered from the reaction mixture by conventional means such as fractional distillation under reduced pressure.

I claim as my invention:

1. A process for the preparation of a biodegradable detergent which comprises the steps of:
   a. condensing butadiene with allyl alcohol in a Diels-Alder reaction at a temperature in the range of from about 50° to about 190° C. and a pressure in the range of atmospheric to about 100 atmospheres to form hydroxymethylcyclohexene;
   b. ring alkylating said hydroxymethylcyclohexene with a 1-alkene in the presence of an organic peroxy free-radical generating compound and hydrogen chloride at a temperature at least as high as the decomposition temperature of said free-radical generating compound;
   c. alkoxylating the resultant n-alkyl-substituted hydroxymethylcyclohexene with an alkoxylating agent selected from the group consisting of ethylene oxide and propylene oxide at a temperature in the range of from about 20° to about 125° C. and a pressure in the range of from about 50 to about 1000 pounds per square inch to form an n-alkyl-substituted hydroxypolyalkoxymethylcyclohexene; and
   d. recovering said n-alkyl-substituted hydroxypolyalkoxymethylcyclohexene.

2. The process as set forth in claim 1 in which said 1-alkene contains from 3 to about 20 carbon atoms.

3. The process as set forth in claim 1 in which said 1-alkene is 1-octene, said alkoxylating agent is ethylene oxide and said n-alkyl-substituted hydroxypolyalkoxymethylcyclohexene is an n-octyl hydroxypolyethoxymethylcyclohexene.

4. The process as set forth in claim 1 in which said 1-alkene is 1-tetradecene, said alkoxylating agent is propylene oxide and said n-alkyl-substituted hydroxypolyalkoxymethylcyclohexene is an n-tetradecyl hydroxypolypropoxymethylcyclohexene.

5. The process as set forth in claim 1 in which said 1-alkene is 1-decene, said alkoxylating agent is ethylene oxide and said n-alkyl-substituted hydroxypolyalkoxymethylcyclohexene is an n-decyl hydroxypolyethoxymethylcyclohexene.

6. The process as set forth in claim 1 in which said 1-alkene is 1-tridecene, said alkoxylating agent is propylene oxide and said n-alkyl-substituted hydroxypolyalkoxymethylcyclohexene is an n-tridecyl hydroxypolypropoxymethylcyclohexene.

7. The process as set forth in claim 1 in which said 1-alkene is 1-dodecene, said alkoxylating agent is ethylene oxide and said n-alkyl-substituted hydroxypolyalkoxymethylcyclohexene is an n-dodecyl hydroxypolyethoxymethylcyclohexene.

* * * * *